United States Patent [19]

Ruschke

[11] Patent Number: 4,521,212

[45] Date of Patent: Jun. 4, 1985

[54] SOLUTION ADMINISTRATION SET

[75] Inventor: Rick R. Ruschke, McHenry, Ill.

[73] Assignee: Baxter Travenol Laboratories, Inc., Deerfield, Ill.

[21] Appl. No.: 404,810

[22] Filed: Aug. 3, 1982

[51] Int. Cl.³ .............................................. A61M 5/14
[52] U.S. Cl. ..................................... 604/126; 604/252
[58] Field of Search ............................... 604/251–256, 604/404, 246, 126; 73/293, 290, 323, 327; 116/227; 55/159

[56] References Cited

U.S. PATENT DOCUMENTS

| | | |
|---|---|---|
| 2,686,428 | 8/1959 | Erikson ................................. 73/293 |
| 3,386,585 | 6/1968 | Weyand et al. . |
| 3,471,019 | 10/1969 | Trasen et al. . |
| 3,658,183 | 4/1972 | Best et al. . |
| 3,782,083 | 1/1974 | Rosenberg . |
| 3,929,157 | 12/1975 | Serur . |
| 3,951,145 | 4/1976 | Smith . |
| 3,954,625 | 5/1976 | Michalski . |
| 3,965,895 | 6/1976 | Dabney . |
| 3,967,620 | 7/1976 | Noiles ................................. 604/251 |
| 4,013,072 | 3/1977 | Jess . |
| 4,113,627 | 9/1978 | Leason . |
| 4,136,693 | 1/1979 | Dyke . |
| 4,173,222 | 11/1979 | Muetterties . |
| 4,256,104 | 3/1981 | Muetterties et al. . |
| 4,318,812 | 3/1982 | Vcelka . |

FOREIGN PATENT DOCUMENTS

| | | |
|---|---|---|
| 831779 | 1/1970 | Canada . |
| 865377 | 5/1941 | France ................................. 604/404 |
| 822195 | 10/1959 | United Kingdom . |
| 2044620 | 10/1980 | United Kingdom . |

OTHER PUBLICATIONS

U.S.S.N. 298,234 (allowed), Herbert Mittleman, Inventor, filed 8/31/81, entitled "Air Bypass Valve Assembly for a Medical Fluid Administration Set.
International Application WO81/02770, Kulle et al,. Inventors, (10/81).
Advertisement, Burron Medical Inc., entitled "The 15 Micron Filtered Drip Chamber from Burron", from Medical Device and Diagnostic Industry, (vol. 6, No. 9, p. 75, Sep. 1984).
Product Code No. 2C2422 sold by Travenol Laboratories, Inc.
Product Code No. 2C0211 sold by Travenol Laboratories, Inc.

Primary Examiner—Stephen C. Pellegrino
Attorney, Agent, or Firm—John P. Kirby, Jr.; Bradford R. L. Price; Garrettson Ellis

[57] ABSTRACT

In a parenteral solution administration set, the porous hydrophilic filter member which can control the liquid level and prevent the passage of gas downwardly through the set can be located adjacent the lower end of the drip chamber to control flow out of the lower end and to be submerged in liquid held in the drip chamber during operation thereof. Significant advantages are obtained. Particularly, the set becomes conveniently usable with parenteral solution pumps. Also the drip chamber may contain an elongated member projecting inwardly of the lower end of the chamber and carrying indicia along its length to indicate liquid volume in the chamber as a function of liquid level.

13 Claims, 10 Drawing Figures

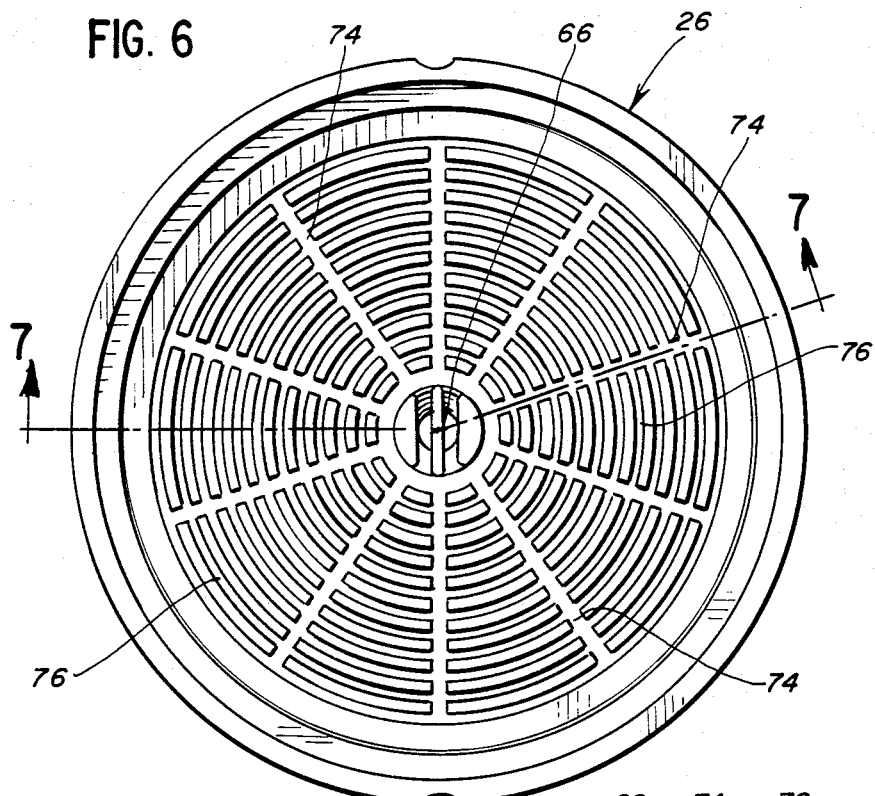
FIG. 6
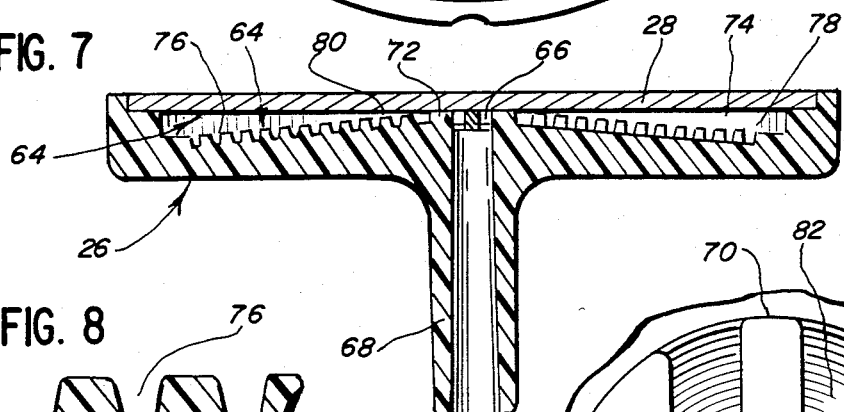
FIG. 7
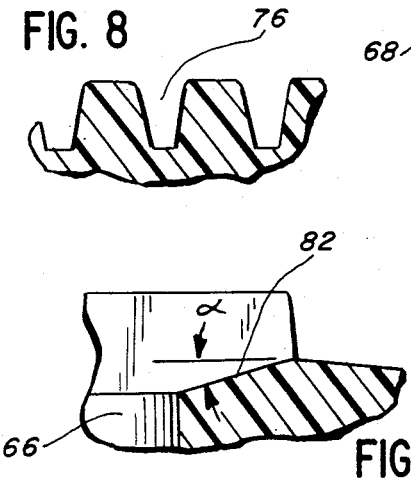
FIG. 8
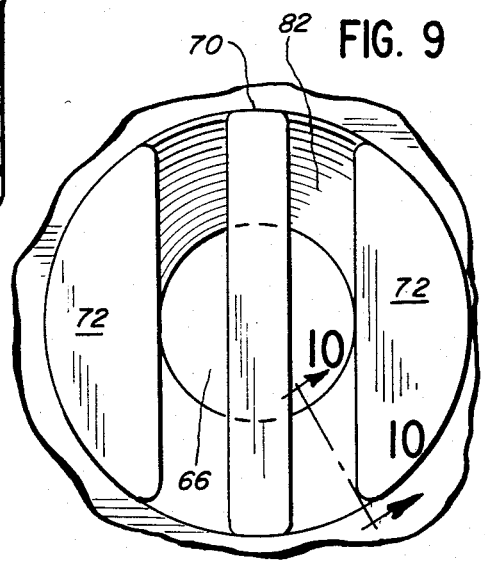
FIG. 9
FIG. 10

SOLUTION ADMINISTRATION SET

TECHNICAL FIELD

This present invention relates to parenteral solution administration to patients, and particularly relates to a parenteral solution administration set which utilizes the known porous, hydrophilic filter member as a liquid level maintaining means, so that the set may be easily utilized to administer repeated measured aliquots of solution to the patient. By this invention, the set can be utilized with a parenteral solution pump.

DESCRIPTION OF PRIOR ART

In Canadian Pat. No. 831,779 a burette-type administration set, adapted for repeated administration of measured liquid aliquots to the patient, utilizes as a liquid level controlling means a porous, hydrophilic filter member. This filter member, having a pore size in the micron range, permits the free passage of aqueous liquids but at the same time prevents the passage of air, due to the capillary film of liquid formed in the pores, which film is formed by capillary attraction. Thus, air is prevented from flowing through the wet membrane, unless the air pressure exceeds the so-called "bubble point", so that at all pressures below a predetermined maximum pressure, air cannot pass through the membrane.

Burette-type solution administration sets are commercially available from Travenol Laboratories, Inc. of Deerfield, Illinois with a typical membrane having a bubble point of 3 to 7 pounds, and a nominal pore size in the hydrophilic membrane of 0.8 micron. This permits operation of the set in the manner described above under normal conditions. The term "nominal pore size" implies that the membrane behaves as if it were a membrane having cylindrical pores of a specified diameter, for example 0.8 micron, although it is recognized that in fact the membrane may have pores of irregular cross sectional shape, or may be a labyrinth of fibers, or the like.

Certain disadvantages exist in burette-type administration sets, particularly in the event that it is desired to use them in conjunction with a parenteral solution pump for administering highly accurate dosages.

For example, if the membrane-carrying administration sets of the prior art run dry and the pump keeps operating, the drip chamber will collapse because the wetted membrane, being normally positioned between the burette chamber and the drip chamber, will not permit air to pass. Following this, upon refilling, the drip chamber can flood in the event that it has been excessively collapsed, and thus become inoperative.

As another problem with the membrane type burette set of the prior art, if the chamber is overfilled, it is not possible to perform the procedure known as "back priming", where one inverts the set to squeeze excess liquid upstream out of the drip chamber and to get air from the burette, to adjust the liquid level in the drip chamber. Because of the presence of the wetted membrane between the drip chamber and the burette chamber, this procedure is normally impossible in conventional versions of the membrane burette set, so that other, more complex procedures are required to adjust the liquid level of the drip chamber.

In accordance with this invention, an improvement is provided in the structure of membrane-type burette sets, in which they exercise their function in the conventional manner of a burette-type set, but at the same time they are capable of being "back primed". Likewise, if they are connected to the pump, and the pump runs the set dry, the drip chamber will not collapse in the manner of the prior art. Instead, the set can be refilled, and it will continue its normal operation without difficulty. Also, they are more easily primed.

Furthermore, by this invention means may be provided for accurate measurement of small fluid volume in a chamber of a solution administration set. This has particular value in the pediatric field for example, for administration of small, carefully measured dosages of critical medication solution.

DESCRIPTION OF THE INVENTION

In this invention a parenteral solution administration set having tubular means for conveying solution from a supply source toward the vascular system of a patient is provided. The set includes a metering chamber for measuring aliquots of solution for administration, plus a drip chamber having upper and lower ends positioned below the metering chamber.

In accordance with this invention the porous hydrophilic filter member described above has a pore size sufficiently small to prevent air at a predetermined maximum pressure from passing through the filter member when wet, while permitting the flow of parenteral solution therethrough. By this invention this filter member is positioned adjacent the lower end of the drip chamber. The effect of this is to cause the filter member to control flow out of the lower end and to be submerged by liquid held in the drip chamber during operation thereof. This permits "back priming" of the set, since there is no air-blocking membrane between the burette chamber and the drip chamber to prevent the exchange of gas therebetween, the liquid level being maintained at the lower end of the drip chamber instead. Likewise, since the bulk of the drip chamber is upstream from the filter membrane, the drip chamber cannot be collapsed by action of the pump when positioned downstream from the drip chamber, when the bubble point of the drip chamber exceeds the pressure-exerting capacity of the pumping system. Thus the drip chamber is protected from being sucked into completely collapsed mode, and the problem of flooding of the drip chamber upon refilling with solution is reduced.

Preferably the filter member of this invention exhibits a bubble point of at least 12 pounds per square inch. The filter member may preferably exhibit a nominal pore size of about 0.6 micron which, in turn, provides a bubble point on the order of 15 pounds per square inch, which has been found to be adequate to perform its intended function in the presence of conventional intravenous solution pumping systems.

The set of this invention thus may be adapted in conventional manner to be operated by a clinical pump for parenteral solution. For example, it may have a segment of collapsible tubing for a roller pump, or it may carry a cassette member for use in a solution pump.

Additionally, this invention relates to a chamber for use in a solution administration set, typically a set for administration of parenteral solution, the chamber having opposed ends. An elongated member projects inwardly of the chamber from adjacent one of the ends. The elongated member carries indicia along its length to indicate liquid volume in the chamber as a function of liquid level when the one end is pointed downwardly.

This arrangement is preferably used in the drip chamber of a solution administration set, typically one intended for use in pediatric cases so that aliquots of 3 or 4 cc. or less may be administered to a child or other patient by use of this volume measuring system in the drip chamber of a set.

The elongated member may comprise a plurality of longitudinally extending vanes which project radially outwardly. The indicia of the elongated member may include step members defined therein at predetermined positions with the liquid volume being determined by comparison of the liquid level with the positions of the step members.

Additionally, the invention of this application relates to a filter for fluids which comprises a filter member and the base upon which the filter member is supported. The base defines a central flow port for receiving filtrate from the filter and conveying it away from the filter member. The base also defines substantially radial flow channels for receiving and conveying filtrate passing through the filter member to the central flow port. By this invention the base defines a filter member-facing surface, peripheral portions of which are spaced from the filter member more than central portions thereof adjacent the flow port. The surface thus defines a slope upwardly and inwardly toward the central flow port. The effect of this is to cause trapped air bubbles on priming of the filter spontaneously to migrate to the central flow port during priming, so that more air bubbles are easily removed from a set incorporating said filter in a spontaneous manner.

BRIEF DESCRIPTION OF THE DRAWINGS

FIG. 6 is an enlarged top plan view of another individual part of the set of FIG. 1 positioned at the bottom of the drip chamber.

FIG. 7 is a sectional view taken along line 7—7 of FIG. 6.

FIG. 8 is a highly enlarged fragmentary view of FIG. 7.

FIG. 9 is a highly enlarged plan view of the central portion of the part of FIG. 6.

FIG. 10 is a highly enlarged fragmentary sectional view taken along line 10—10 of FIG. 9.

DESCRIPTION OF SPECIFIC EMBODIMENT

Figure 1:
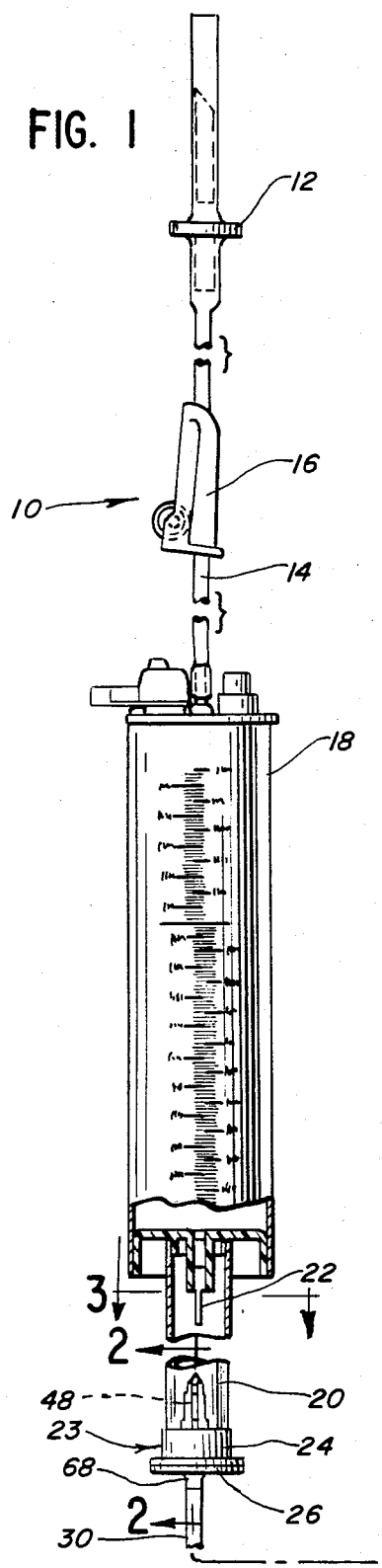
FIG. 1 is an elevational view of a burette-type solution administration set for the purpose of conveying solution from a supply source to the vascular system of a patient, typically by way of an intravenous needle, or by connection to another set for a pump.
Figure 2:
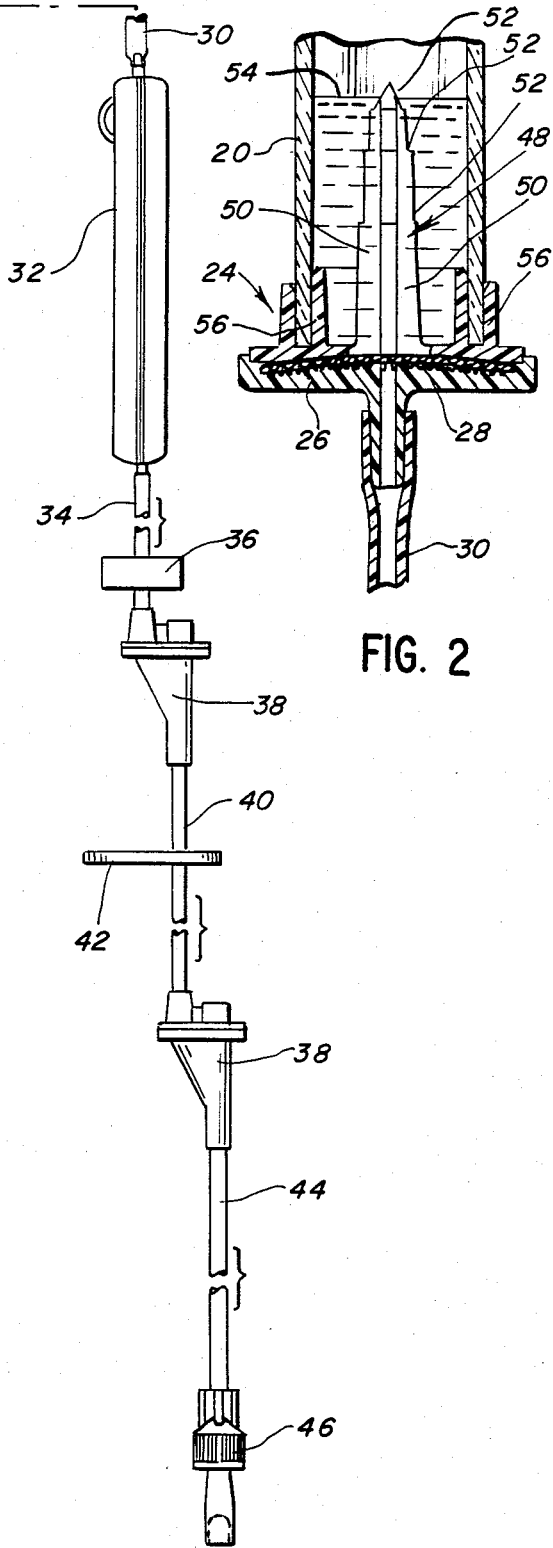
FIG. 2 is an enlarged fragmentary sectional view taken in longitudinal section along line 2—2 of FIG. 1.

Referring to the drawings and in particular to FIG. 1, a solution administration set 10 of the burette type is disclosed.

As shown therein, conventional spike 12 is provided at one end of set 10 for connection with a source of parenteral solution. Tubing 14 carries a conventional roller clamp 16 for flow control, and leads into burette chamber 18, which may be of overall conventional design. For example chamber 18 may be of the overall type of burette chamber commercially available in some solution administration sets sold by Travenol Laboratories, Inc. of Deerfield, Illinois, but without valve means at the bottom, so that flow through the burette chamber is freely permitted.

Carried at the bottom end of burette chamber 18 is drip chamber 20, having conventional drop forming means 22 at its upper end. A filter housing 23 is positioned at the lower end of drip chamber 20 comprising upper housing member 24 and lower housing member 26, with a porous hydrophilic filter 28 of the type previously described being carried between the two housing members 24, 26. These, in turn, may be sealed together by adhesive, or by sonic sealing in the preferred event that they are made of an appropriate thermoplastic material.

Below housing members 24, 26 is another segment 30 of tubing which carries roller clamp 32 which is especially designed for accurate flow, and which may include a captured length of silicone tubing inside of its housing in the manner, for example, described in International Application (PCT) Publication No. WO81/02770.

Below this, another segment of tubing 34 is provided. Tubing 34 may constitute compressable tubing for a roller pump system, so that tubing 34 may be fitted into roller type pump system 36, shown schematically, for precise flow control of solution through set 10.

A pair of injection sites 38 are provided, separated by tubing 40, which carries slide clamp 42. Below this, tubing segment 44 is provided, and an end connector 46 which may be used for connection to a pump of conventional design, or to another set, for ultimate communication with the vascular system of a patient.

Upper housing member 24 further may carry an elongated member 48, which may be an integral part of molded, upper housing member 24 and which projects inwardly of drip chamber 20 from its lower end. Elongated member 48 includes a plurality of (specifically four) longitudinally extending vanes 50 positioned approximately 90° apart from each other in the specific embodiment and carrying the indicia previously described. Specifically, the indicia can include step members 52 which indicate residual liquid volume in drip chamber 20 when the liquid level 54 is adjacent one of step members 52, so that the final measurement of individual ml. of liquid can be provided as the drip chamber is drained.

Upper housing member 24 also provides a pair of telescoping flanges 56 defining an annular space between them into which the tubular portion of drip chamber 20 can be placed in sealing relation. The upper surface of one of these flanges 56 can serve as a liquid level measuring index as well, for example at the 1 ml. level, in cooperation with steps 52 which then may represent the 2 ml. and 3 ml. volumes, for example.

Figure 3:
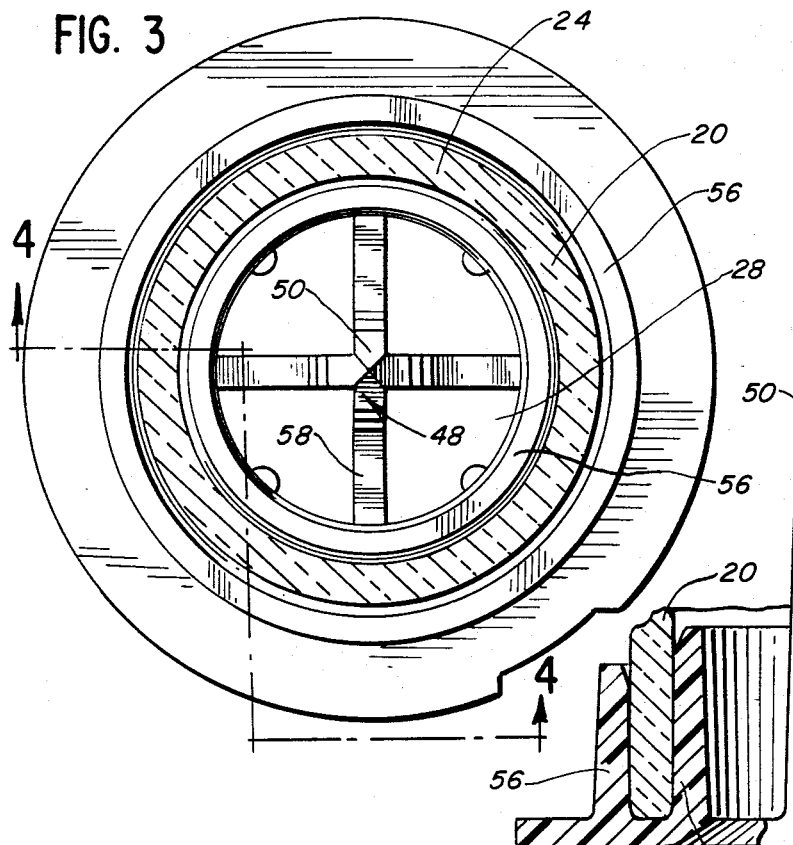
FIG. 3 is an enlarged sectional view taken along line 3—3 of FIG. 1.

FIG. 3 is a sectional view, looking downwardly at upper housing part 24 and hydrophilic filter member 28. Projecting member 48, defining the individual vanes 50, is also shown, and the apertures which permit liquid to flow against membrane 28 for passage therethrough can also be seen. Specifically, projecting member 48 can be supported by struts 58 which connect with the remainder of the body of upper housing member 24, also connecting to one of the sleeves 56.

Figure 4:
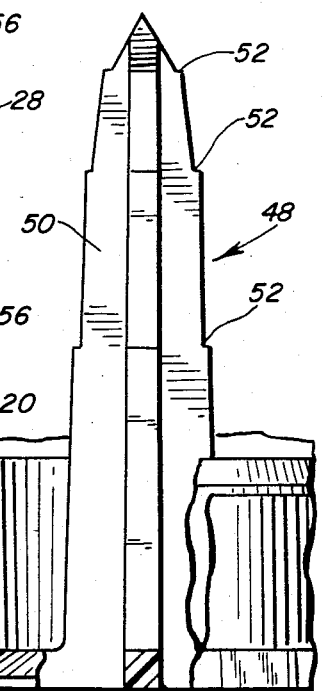
FIG. 4 is an enlarged fragmentary sectional view taken along line 4—4 of FIG. 3.

FIG. 4 also shows further details of upper housing 24. In FIG. 4, energy-directing ridge 60 is shown, which facilitates the sonic welding of upper housing 24 to lower housing 26, but in actuality it no longer exists in the same form after assembly of the parts, and is shown in FIG. 4 for purposes of illustration.

Figure 5:
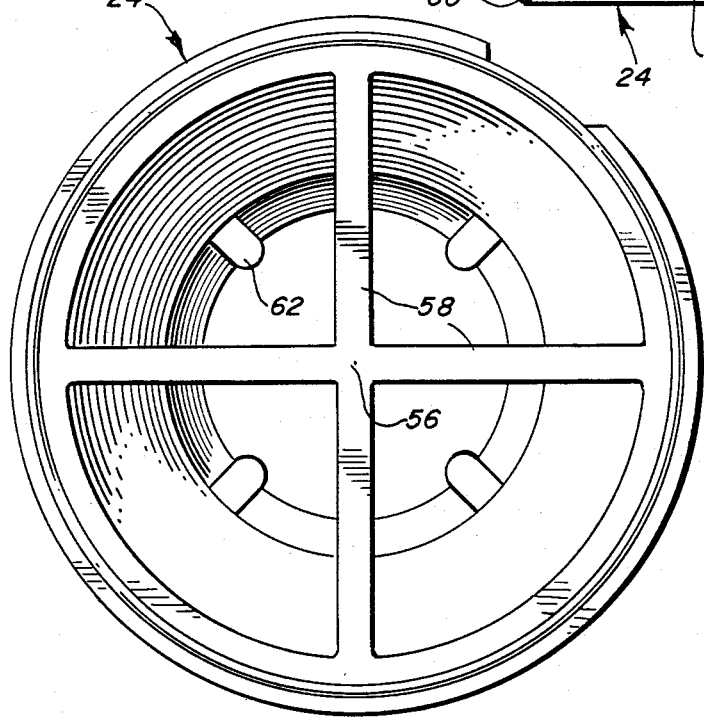
FIG. 5 is a bottom plan view of an individual part at the bottom end of the drip chamber of the set of FIG. 1.

FIG. 5 is a bottom plan view of upper housing member 24, with struts 58 being shown, as well as projections 62 which serve to help retain membrane 28 in a position between upper housing member 24 and lower housing member 26.

FIGS. 6–10 show lower housing member 26 and details of its construction. Lower housing member 26 defines a base 64 upon which filter membrane 28 is supported. Base 64 (and housing member 26) define a central flow port 66 for receiving filtrate from filter 28 and conveying it away from the filter through port 68. Flow port 66 is bridged over by a baffle member 70 and is bracketed between added baffle members 72.

Base 64 defines substantially radial flow channels 74, each of which preferably terminates at its inner end in flow facing relation with one of baffle members 70 or 72. Added circumferential channels 76 are also provided so that the base 64 is a fairly complex structure of interconnecting flow channels as disclosed in FIGS. 6 and 7.

As shown therein, base 64 defines a filter member-facing surface having peripheral portions 78 which are spaced from filter member 28 more than central portions 80 thereof, adjacent flow port 66. Accordingly, radial flow channels 74 slope upwardly as they extend inwardly toward central flow port 66. An advantage of this construction is that, when set 10 is primed for use, solution tends to spontaneously flow into the peripheral sections of the filter defined by housing part 26, and particularly the space between filter membrane 28 and face 64. Air bubbles, on the other hand, spontaneously flow upwardly and inwardly along radial channels 74, to be flushed through aperture 66 and down through the set, for better priming with fewer residual bubbles remaining trapped in set 10. Downwardly sloping annular surface 82 is provided in lower housing member 26 immediately adjacent to aperture 66 as shown in FIGS. 9 and 10.

As the result of this, the set of this invention can be easily primed and can be used to provide many measured aliquots of solution sequentially and intermittently to a patient by filling burette chamber 18, and then allowing it to drain. In this embodiment, drip chamber 20 can drain as well, with flow being spontaneously controlled by porous hydrophilic filter member or membrane 28 through which air cannot pass. The system can then be easily refilled, filling the drip chamber 20 by the conventional expedient of priming in the manner of a conventional solution administration set, and refilling the burette chamber 18 to the desired level.

The set of this invention may be used in conjunction with a pump, either pump 36 or a pump to which the set 10 connects at its connector 46, the system operating without collapsing of drip chamber 20 when it runs dry, since air from the drip chamber cannot pass through filter member 28, assuming that its "bubble point" is not exceeded. Likewise the set of this invention can be back primed, i.e., excess liquid in drip chamber 20 can be returned to burette chamber 18, to easily achieve a desired liquid level in the drip chamber without the need for a complex procedure.

The above has been offered for illustrative purposes only, and is not intended to limit the scope of the invention of this application, which is as defined in the claims below.

That which is claimed is:

1. A parenteral solution administration set having tubular means for conveying solution from a supply source toward the vascular system of a patient, comprising:
    a metering chamber measuring aliquots of solution for administration;
    a drip chamber connected to said metering chamber and having upper and lower ends positioned below said metering chamber;
    said drip chamber including, at its lower end, a porous, hydrophilic filter member having a pore size sufficiently small to prevent air at a predetermined maximum pressure from passing through said filter member when wet, while permitting the flow of parenteral solution therethrough, said filter member being operative at the lower end of the drip chamber to control flow out of said lower end and to be submerged by liquid held in the drip chamber during operation thereof;
    said metering chamber and drip chamber being free of any air-blocking membrane therebetween, whereby back priming of the set is enabled.

2. The set of claim 1 in which said filter member exhibits a "bubble point" of at least 12 lb/in$^2$.

3. The set of claim 2 in which said filter member exhibits a nominal pore size of about 0.6 micron.

4. The set of claim 1, having means permitting use with a clinical pump for parenteral solution.

5. A filter for fluids which comprises a filter member and a base upon which said filter member is supported, said base defining a central flow port for receiving filtrate from the filter and conveying it away from the filter member, said base also defining substantially radial flow channels for receiving and conveying filtrate passing through the filter member to the central flow port, the improvement comprising, in combination:
    said base defining a filter member-facing surface, peripheral portions of said surface being spaced from the filter member more than central portions thereof adjacent the flow port, said surface defining a slope upwardly and inwardly toward said central flow port to cause trapped air bubbles on priming spontaneously to migrate to the central flow port.

6. In a parenteral solution administration set having tubular means for conveying solution from a supply source to the vascular system of a patient, and including a metering chamber for measuring aliquots of solution for administration, plus a drip chamber having upper and lower ends positioned below said metering chamber, the improvement comprising, in combination:
    a porous hydrophilic filter member having a pore size sufficiently small to prevent air at a predetermined maximum pressure from passing through said filter member when wet, while permitting the flow of parenteral solution therethrough, said filter member being positioned adjacent the lower end of the drip chamber to control flow out of said lower end then to be submerged by liquid held in the drip chamber during operation thereof;
    said filter member being supported on a base, said base defining a central flow port for receiving filtrate from the filter and conveying it away from the filter member, said base also defining substantially radial flow channels for receiving and conveying filtrate passing through the filter member to the central flow port, said base defining a filter member-facing surface, peripheral portions of said surface being spaced from the filter member more than central portions thereof adjacent the flow port, said surface defining a slope upwardly and inwardly toward said central flow port to cause trapped air bubbles on priming spontaneously to migrate to the central flow port.

7. The set of claim 6 in which said filter member exhibits a "bubble point" of at least 12 pounds per square inch, and having means permitting use with a clinical pump for parenteral solution.

8. The filter of claim 7 in which said drip chamber carries at its lower end an elongated member projecting inwardly of said drip chamber, said elongated member carrying indicia along its length to indicate liquid volume in said drip chamber as a function of liquid level.

9. The solution administration set of claim 8 in which the indicia of said elongated member includes step members defined therein at predetermined positions.

10. The solution administration set of claim 9 in which said elongated member comprises a plurality of longitudinally extending vanes which project radially outwardly.

11. The solution administration set of claim 10 in which said filter member exhibits a nominal pore size of about 0.6 micron.

12. A parenteral solution administration set in integral, unitary form, having tubular means for conveying solution from a supply source toward the vascular system of a patient, comprising:
   a metering chamber for measuring aliquots of solution for administration;
   a drip chamber integrally connected to said metering chamber having upper and lower ends positioned below said metering chamber;
   said drip chamber including, adjacent its lower end, a porous, hydrophilic filter member having a pore size sufficiently small to prevent air at a predetermined maximum pressure from passing through said filter member when wet, while permitting the flow of parenteral solution therethrough, said filter member being operative to control flow out of said lower end and to be submerged by liquid held in the drip chamber during operation thereof;
   said metering chamber and drip chamber being free of any air-blocking membrane therebetween, whereby back priming of the set is enabled.

13. In a medical solution administration set having a spike, an end connector and tubular means connected to and between said spike and said end connector for conveying solution from a supply source toward the vascular system of the patient, the improvement comprising:
   a chamber connected to said tubular means, between said spike and said end connector, said chamber including opposed ends;
   an elongated member projecting inwardly of said chamber from adjacent one of said ends, and including a plurality of longitudinally extending vanes which project radially outwardly; and
   indicia carried along the length of said elongated member to indicate liquid volume in said chamber as a function of liquid level when said one end is pointed downwardly, said indicia including step members carried by said elongated member.

* * * * *